United States Patent
Khalde et al.

(10) Patent No.: US 9,863,860 B2
(45) Date of Patent: Jan. 9, 2018

(54) METHODS AND APPARATUS FOR MEASURING RHEOLOGICAL PROPERTIES OF MULTI-PHASE FLUIDS

(71) Applicant: INDIAN INSTITUTE OF TECHNOLOGY MADRAS, Chennai, Tamil Nadu (IN)

(72) Inventors: Chirag Khalde, Talegaon Dabhade (IN); Jitendra Sangwai, Mehekar (IN)

(73) Assignee: INDIAN INSTITUTE OF TECHNOLOGY MADRAS, Chennai (IN)

( * ) Notice: Subject to any disclaimer, the term of this patent is extended or adjusted under 35 U.S.C. 154(b) by 0 days.

(21) Appl. No.: 14/914,499

(22) PCT Filed: Aug. 12, 2014

(86) PCT No.: PCT/IB2014/063868
§ 371 (c)(1),
(2) Date: Feb. 25, 2016

(87) PCT Pub. No.: WO2015/028910
PCT Pub. Date: Mar. 5, 2015

(65) Prior Publication Data
US 2016/0216188 A1    Jul. 28, 2016

(30) Foreign Application Priority Data
Aug. 26, 2013 (IN) ........................................ 3777/13

(51) Int. Cl.
*G01N 11/14*    (2006.01)
*G01N 33/28*    (2006.01)
(Continued)

(52) U.S. Cl.
CPC ............. *G01N 11/14* (2013.01); *G01N 33/28* (2013.01); *G01N 33/2823* (2013.01); *F04C 2/16* (2013.01);
(Continued)

(58) Field of Classification Search
CPC .. G01N 11/14; G01N 33/28; G01N 2011/002; G01N 33/2823; F04C 11/001; F04C 14/02; F04C 14/26; F04C 2/16
(Continued)

(56) References Cited

U.S. PATENT DOCUMENTS

| 4,095,461 A | 6/1978 | Starita |
| 4,638,668 A | 1/1987 | Leverberg et al. |

(Continued)

FOREIGN PATENT DOCUMENTS

| CH | 683322 A5 | 2/1994 |
| GB | 660662 A | 11/1951 |

(Continued)

OTHER PUBLICATIONS

International Search Report and Written Opinion for International Application No. PCT/IB14/60545, dated Sep. 10, 2014.
(Continued)

*Primary Examiner* — Randy Gibson
*Assistant Examiner* — Gedeon M Kidanu
(74) *Attorney, Agent, or Firm* — Maschoff Brennan

(57) ABSTRACT

An apparatus for measuring rheological properties of a multi-phase fluid is provided. The apparatus includes a static chamber configured to contain a multi-phase fluid having at least a first phase and a second phase. The apparatus also includes a rotor member submersed in the multi-phase fluid in the static chamber. The rotor member is rotatable about a horizontal rotational axis within the static chamber and the
(Continued)

static chamber and the rotor member are oriented in a substantially horizontal direction.

25 Claims, 4 Drawing Sheets

(51) Int. Cl.
    *F04C 11/00*     (2006.01)
    *F04C 14/02*     (2006.01)
    *F04C 14/26*     (2006.01)
    *F04C 2/16*     (2006.01)
    *G01N 11/00*     (2006.01)

(52) U.S. Cl.
    CPC ............. *F04C 11/001* (2013.01); *F04C 14/02* (2013.01); *F04C 14/26* (2013.01); *G01N 2011/002* (2013.01)

(58) Field of Classification Search
    USPC ........................ 73/54.01–54.02, 54.23, 54.28
    See application file for complete search history.

(56) References Cited

U.S. PATENT DOCUMENTS

| | | | |
|---|---|---|---|
| 4,643,021 A | 2/1987 | Mattout | |
| 4,684,072 A * | 8/1987 | Nelson | B02C 17/04 241/171 |
| 4,878,377 A * | 11/1989 | Abel | G01N 11/14 73/54.32 |
| 4,974,446 A | 12/1990 | Vigneaux | |
| 5,209,108 A * | 5/1993 | Shackelford | E21B 43/26 73/54.28 |
| 5,348,453 A * | 9/1994 | Baran | B29C 47/0845 417/440 |
| 5,365,777 A | 11/1994 | Layton | |
| 5,691,560 A | 11/1997 | Sakakibara | |
| 5,728,951 A | 3/1998 | Van Cleve et al. | |
| 6,135,723 A * | 10/2000 | Hatton | F04C 2/16 417/251 |
| 6,234,030 B1 * | 5/2001 | Butler | E21B 21/01 73/195 |
| 6,629,451 B1 * | 10/2003 | Taylor | G01N 11/14 73/54.28 |
| 6,742,774 B2 | 6/2004 | Holl | |
| 6,874,353 B2 | 4/2005 | Johnson et al. | |
| 6,959,588 B2 | 11/2005 | Zougari et al. | |
| 6,971,262 B1 | 12/2005 | Marchal et al. | |
| 6,997,045 B2 | 2/2006 | Wallevik et al. | |
| 7,017,393 B2 | 3/2006 | Doe et al. | |
| 7,021,123 B2 | 4/2006 | Wallevik et al. | |
| 7,581,436 B2 | 9/2009 | Eskin et al. | |
| 8,024,962 B2 | 9/2011 | Tonmukayakul et al. | |
| 8,794,051 B2 * | 8/2014 | Morgan | G01N 11/14 73/54.01 |
| 2002/0004176 A1 * | 1/2002 | Tanabe | G03G 9/0804 430/137.14 |
| 2003/0154772 A1 | 8/2003 | Jackson | |
| 2003/0192366 A1 | 10/2003 | Taylor | |
| 2005/0170516 A1 | 8/2005 | Kharrat et al. | |
| 2009/0133478 A1 * | 5/2009 | Sentmanat | G01N 11/14 73/54.28 |
| 2011/0020162 A1 | 1/2011 | Izawa et al. | |
| 2011/0061451 A1 | 3/2011 | Harris et al. | |
| 2011/0123378 A1 | 5/2011 | Kothnur et al. | |
| 2011/0293441 A1 * | 12/2011 | Anderson | F01C 21/002 417/279 |
| 2013/0136639 A1 * | 5/2013 | Simpson | F04D 3/02 418/1 |

FOREIGN PATENT DOCUMENTS

| | | |
|---|---|---|
| GB | 711851 A | 7/1954 |
| WO | 2008154035 A1 | 12/2008 |

OTHER PUBLICATIONS

International Search Report and Written Opinion for International Application No. PCT/IB14/63868, dated Feb. 6, 2015.
Lord, D.L., "Helical Screw Rheometer: A New Tool for Stimulation Fluid Evaluation," Society of Petroleum Engineers, pp. 1-7 (Oct. 2, 1988).
Lord, D.L., and Shackelford, D., "Application Of Helical Screw Rheometer for Rheological Measurements," Petroleum Society of Canada, vol. 29, Issue 3, pp. 1-6 (May 1990).
Extended European Search Report for European International Application No. 14782984.0 dated Dec. 1, 2016, pp. 9.

* cited by examiner

METHODS AND APPARATUS FOR MEASURING RHEOLOGICAL PROPERTIES OF MULTI-PHASE FLUIDS

CROSS-REFERENCE TO RELATED APPLICATIONS

This Application is the U.S. National Stage filing under 35 U.S.C. §371 of International Application No. PCT/IB2014/063868 filed on Aug. 12, 2014, which claims priority of India Patent Application No. 3777/CHE/2013 filed on Aug. 26, 2013.

BACKGROUND

Various types of fluids are used in applications in the oil and gas industry, paint industry, plastics industry, pharmaceutical industry, and others. Understanding rheology of emulsions, slurries and suspensions is desirable in these applications. Typically, as two or more immiscible fluids flow through a pipeline, reactor, column, and so on, the mixing of the fluids varies at different locations within the system due in part to varying shear rates. This flow phenomenon may result in formation of emulsions and suspensions that are substantially stable in shear environment but may separate out into their constituents as the effect of shear is reduced. It is desirable to determine in-situ rheological properties, such as viscosity for such fluid systems, to appropriately design a part or the whole of a system accordingly.

Conventional techniques for measuring the rheological properties of multi-phase fluids such as emulsions and slurries include mixing them in a separate pre-mixer. The emulsion formed after the mixing is subsequently transferred to a cup and bob assembly of a rheometer and the viscosities may be measured using the rheometer for different shear rates. However, mixing of the fluids using the conventional cup and bob systems is sometimes poor, especially at low shear rates. Moreover, pre-mixed emulsions are often substantially unstable. Furthermore, in a conventional, vertical cup and bob rheometer, shearing takes place in a direction normal to the spin axis of the cup and bob assembly (and tangential to an infinite series of circles concentric with the cup/bob). Radial mixing is usually not expected in such scenarios. In certain cases, if multi-phase fluids are used, the fluids may also not mix with one another due to variation in the densities of the fluids resulting in settling, with the densest fluid at the bottom, and the lightest fluid at the top, thereby resulting in inaccurate measurements.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

Briefly, in accordance with one aspect, an apparatus for measuring rheological properties of a multi-phase fluid is provided. The apparatus includes a static chamber configured to contain a multi-phase fluid having at least a first phase and a second phase. The apparatus also includes a rotor member submersed in the multi-phase fluid in the static chamber. The rotor member is rotatable about a horizontal rotational axis within the static chamber. The static chamber and the rotor member are oriented in a substantially horizontal direction.

In accordance with another aspect, an apparatus for measuring rheological properties of a multi-phase fluid is provided. The apparatus includes a static chamber configured to contain a multi-phase fluid having at least a first phase and a second phase. The apparatus also includes a rotor member submersed in the multi-phase fluid in the static chamber and rotatable about a rotational axis within the static chamber to apply a shear stress to the multi-phase fluid in a plane normal to the rotational axis. The static chamber and the rotor member are oriented in a substantially horizontal direction. The apparatus further includes a processing circuitry configured to estimate the rheological properties of the multi-phase fluid as the rotor member is rotated within the static chamber.

In accordance with another aspect, a method for measuring rheological properties of a multi-phase fluid is provided. The method includes providing a static chamber having a rotor member. The static chamber and the rotor member are oriented in a substantially horizontal direction. The method includes placing a multi-phase fluid having a first phase and a second phase within the static chamber. The method also includes rotating the rotor member about a horizontal rotational axis within the static chamber to apply shear stress to the multi-phase fluid in a plane normal to the rotational axis.

DETAILED DESCRIPTION

Figure 1:
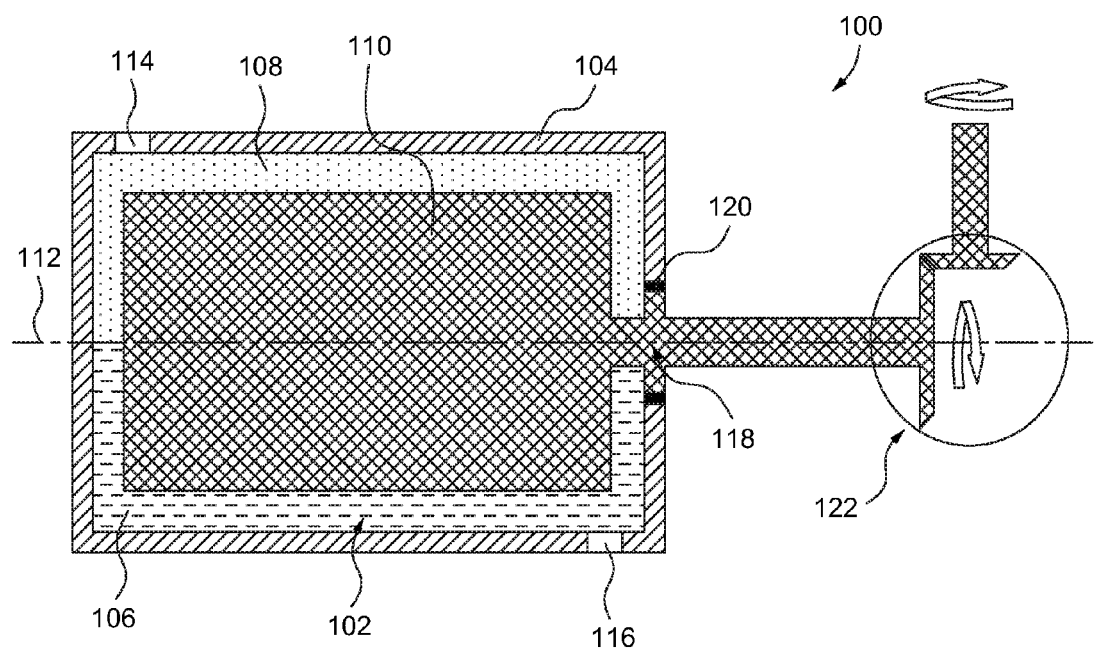
FIG. 1 is an example apparatus for measuring rheological properties of a multi-phase fluid.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

It will also be understood that any compound, material or substance which is expressly or implicitly disclosed in the specification and/or recited in a claim as belonging to a group or structurally, compositionally and/or functionally related compounds, materials or substances, includes individual representatives of the group and all combinations thereof. While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

Some embodiments are generally directed to techniques of measuring rheological properties of multi-phase fluids like emulsions, slurries and suspensions such as used in oil and gas, paint, polymer and pharmaceutical industries. The embodiments described below provide an apparatus that enhances mixing of multi-phase fluids and facilitates accurate measurement of rheological properties of fluids. The proposed technique can be used for rheological measurements of complex fluids at high pressure and high temperature conditions such as required in oil and gas industries.

The proposed apparatus includes a horizontally oriented static chamber and a rotor member that is used for mixing fluids within the static chamber. As the rotor member rotates about a horizontal rotational axis within the static chamber that contains the fluids, the molecules of different fluids close to the surface of rotor member experience a no-slip condition. The molecules of the fluids move along with the rotor member. Thus, each fluid layer tends to mix well with the adjacent fluids as the rotor member rotates. The application of shear stress to the fluids through horizontally oriented rotor member results in enhanced mixing even at substantially low shear rates as compared to conventional vertical cup and bob rheometers.

Referring now to FIG. 1, an example, apparatus 100 for measuring rheological properties of a multi-phase fluid 102 is provided. The apparatus includes a static chamber 104 configured to contain the multi-phase fluid 102 having at least a first phase 106 and a second phase 108. The apparatus also includes a rotor member 110 submersed in the multi-phase fluid 102. The rotor member is rotatable about a horizontal axis 112 within the static chamber 104. In the illustrated embodiment, the static chamber 104 and the rotor member 110 are oriented in a substantially horizontal direction. In this example embodiment, the static chamber 104 and the rotor member 110 are arranged to be coaxial.

In certain embodiments, the multi-phase fluid 102 includes at least two immiscible fluids. In one example, the two immiscible fluids are oil and water. In one example embodiment, the first phase 106 of the multi-phase fluid 102 is a liquid and the second phase 108 is a gas. In another example embodiment, the first phase 106 of the multi-phase fluid 102 is a solid and the second phase 108 is a liquid. In certain embodiments, the multi-phase fluid 102 may include more than two phases. For example, the first phase 106 of the multi-phase fluid 102 can include a liquid, the second phase 108 can include a solid and a third phase (not shown) of the multi-phase fluid 102 can be a gas.

The static chamber 104 may be formed of a variety of materials, such as metal, steel, stainless steel, hastelloy, titanium, aluminum, quartz, optical glass, inconel, acrylic, or combinations thereof. However, a variety of other materials may be used for the static chamber 104. The static chamber 104 can generally be of any size. The size of the static chamber 104 may be selected based upon viscosity of the multi-phase fluid 102, density of the multi-phase fluid 102, an applied shear rate, or combinations thereof. In one example embodiment, the diameter of the static chamber 104 is about 30 mm to about 90 mm. Specific examples of the diameter include about 30 ram, about 35 mm, about 40 mm, about 45 mm, about 50 mm, about 55 mm, about 60 mm, about 65 mm, about 70 mm, about 75 mm, about 80 mm, about 85 mm, about 90 mm and ranges between any two of these values (including endpoints).

The static chamber 104 may include at least one inlet port 114 and at least one outlet port 116. The multi-phase fluid 102 is filled into the horizontally oriented static chamber 104 through the inlet port 114 while the outlet port 116 can be closed during the filling of the multi-phase fluid 102. Further, the multi-phase fluid 102 may be removed from the static chamber 104 through the outlet port 116. In certain embodiments, injectors or a funnel may be used to fill viscous fluids into the static chamber 104. As the multi-phase fluid 102 is filled into the static chamber 104, the multiple phases of the multi-phase fluid 102 form a layer one above another with the lighter fluid at the top owing to immiscible nature of these phases in un-shearing environment.

The rotor member 110 may be formed of a variety of materials, such as metal, steel, stainless steel, hastelloy, titanium, aluminum, quartz, optical glass, inconel, acrylic, or combinations thereof. Other suitable materials may be used for the rotor member 110. The rotor member 110 may generally be of any size. The rotor member 110 may be designed based on DIN standards (DIN 53019 and 53018) and can have a diameter of about 10 mm to about 90 mm. Specific examples of the diameter include about 10 mm, about 20 mm, about 30 mm, about 40 mm, about 50 mm, about 60 mm, about 70 mm, about 80 mm, about 90 mm, and ranges between any two of these values (including endpoints). The length of the rotor member 110 may be about three times the radius of the rotor member 110. In some examples, a ratio of the radius of the static chamber 104 to radius of the rotor member 110 is about 1.1. In certain examples, the diameter of the static chamber 104 is up to about 60 mm and the diameter of the rotor member 110 is about 50 mm.

The apparatus 100 may include at least one motor (not shown) configured to rotate the rotor member 110 about the horizontal rotational axis 112 within the static chamber 104. In some example embodiments, a speed of rotation of the rotor member 110 is about 0.01 revolutions per minute (rpm) to about 10000 rpm, about 1 rpm to about 1,000 rpm, or about 10 rpm to about 100 rpm. Specific examples of speed of rotation include about 0.01 rpm, about 0.1 rpm, about 1 rpm, about 10 rpm, about 100 rpm, about 1,000 rpm, about 5,000 rpm, about 10,000 rpm, and ranges between any two of these values (including endpoints). In some examples, an applied shear rate is about $10^{-5}$ s$^{-1}$ to about $10^7$ s$^{-1}$. In some examples, the applied shear rate is about $10^{-2}$ s$^{-1}$ to about $10^3$ s$^{-1}$. In certain embodiments, a degree of mixing of the first phase 104 and the second phase 106 is about 1% to about 95%, and ideally 100%. Specific examples of the degree of mixing for first phase and second phase include about 1%, about 10%, about 20%, about 30%, about 40%, about 50%, about 60%, about 70%, about 80%, about 90%, about 95%, and ranges between any two of these values (including endpoints).

In some embodiments, the rotor member 110 is supported by one or more bearings 118 within the static chamber 104. Further, a sealing mechanism generally represented by reference numeral 120 may be used to prevent leakage of the multi-phase fluid 102 from the static chamber 104. In some examples, rotation to the rotor member 110 may be provided through a gearing mechanism. For example, a bevel gear 122 may be used to transfer plane of rotation with conventional motor arrangement.

In some example embodiments, a clearance between the static chamber 104 and the rotor member 110 is selected based upon the type of the multi-phase fluid 102, size of the static chamber 104, size of the rotor member 110, or combinations thereof. For example, in multi-phase fluids flowing in a substantially large diameter pipe where the extensional flow dominates the shear flow, a substantially large clearance between the static chamber 104 and the rotor member 110 may be selected.

Alternately, in multi-phase fluids where shear flow dominates the extensional flow (for example, complex pipe flow in substantially small diameter pipe with relatively small Reynolds number), a substantially small clearance between the static chamber 104 and the rotor member 110 may be used. In one example embodiment, the clearance between the static chamber 104 and the rotor member 110 is about 1 mm to about 50 mm. Specific examples of the clearance between the static chamber 104 and the rotor member 110 include about 1 mm, about 5 mm, about 10 mm, about 15 mm, about 20 mm, about 25 mm, about 30 mm, about 35 mm, about 40 mm, about 45 mm, about 50 mm, and ranges between any two of these values (including endpoints).

In operation, as the rotor member 110 rotates about the horizontal rotational axis 112 within the static chamber 104, the rotor member 110 shears the multi-phase fluid 102 in a plane normal to the rotational axis 112. The rotation of the rotor member 110 facilitates mixing of multiple phases such as the first phase 106 and the second phase 108 of the multi-phase fluid 102 even at a low shear rate, starting at the boundary between the phases in case of horizontal rotation of the rotor member 110. The molecules of different phases such as the first phase 106 and the second phase 108 proximate to the surface of rotating bob experience a no-slip condition and travel along with rotor member 110. This happens for each phase layer and therefore each phase mixes with the adjacent phases of the multi-phase fluid 102 as the rotor member 110 rotates about the axis 112.

The apparatus 100 further includes a processing circuitry (not shown) configured to estimate the rheological properties of the multi-phase fluid 102 based on an applied shear rate, temperature of the multi-phase fluid 102, pressure of the multi-phase fluid 102, or combinations thereof. Examples of the rheological properties of the multi-phase fluid 102 include, but are not limited to, a viscosity ($\eta$), a shear storage modulus (G'), a shear loss modulus (G"), or combinations thereof. In certain embodiments, the apparatus 100 can be used to estimate the rheological properties of fluids having a viscosity of about $10^{-4}$ Pascal second (Pa·s) to about $10^{10}$ Pa·s. Specific examples of the viscosity of such fluids include about $10^{-4}$ Pa·s, about $10^{-2}$ Pa·s, about 10 Pa·s, about $10^2$ Pa·s, about $10^4$ Pa·s, about $10^6$ Pa·s, about $10^8$ Pa·s, about $10^{10}$ Pa·s, and ranges between any two of these values (including endpoints).

A variety of configurations of the apparatus 100 described above may be envisaged. For example, the rotor member 110 may include a plurality of threads (not shown) formed on a first surface of the rotor member 110 to facilitate mixing of the first phase 106 and the second phase 108 of the multi-phase fluid 102. In another example, the apparatus 100 may include the static chamber 104 with a plurality of threads formed on an inner surface of the static chamber 104 and the rotor member 110 having a smooth surface. In another example embodiment, the static chamber 104 containing the multi-phase fluid 102 is rotated about the rotational axis 112 and the rotor member 110 is kept stationary within the rotating static chamber 104.

In certain embodiments, the apparatus 100 can include double or multiple start threads on each of the static chamber 104 and the rotor member 110. Further, the apparatus 100 may be used for parallel plate geometry, cone geometry and plate geometry. The apparatus 100 can also be used for double gap geometry with proposed threading on the rotor member 110, the static chamber 104, or both. In another embodiment, the rotor member is rotated about an axis of eccentric rotation to facilitate mixing of multi-phase fluid 102. In certain embodiments, the static chamber 104 and/or the rotor member 110 may have a rough surface. In some examples, a relative roughness defined by a ratio of a measured roughness to a diameter of the static chamber 104 and/or the rotor member 110 is about $10^{-5}$ to about 0.5.

In the illustrated embodiment, the apparatus 100 does not require a pre-mixer for mixing the first phase 106 and the second phase 108. Further, the apparatus 100 facilitates formation of an emulsion or suspension even at low shearing rates.

Figure 2:
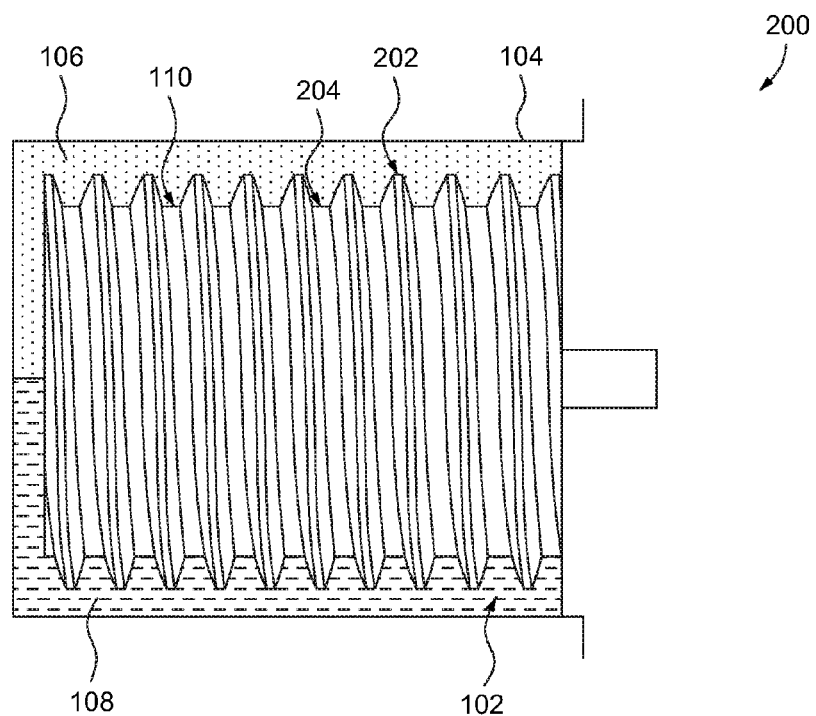
FIG. 2 illustrates an example configuration of the apparatus of FIG. 1.

FIG. 2 illustrates an example configuration 200 of the apparatus 100 of FIG. 1. As illustrated, the apparatus 200 includes a static chamber 104 configured to contain the multi-phase fluid 102 and a rotor member 110 submersed in the multi-phase fluid 102. The axes of the static chamber 104 and the rotor member 110 are oriented in a substantially horizontal direction. The multi-phase fluid 102 includes the first phase 106 and the second phase 108. The multi-phase fluid 102 can include more than two phases.

In the illustrated embodiment, the rotor member 110 includes a plurality of threads generally represented by reference numeral 202 formed on a first surface 204 of the rotor member 110 that is submersed in the multi-phase fluid 102. The plurality of threads 202 are configured to facilitate mixing of the fluids such as the first phase 106 and the second phase 108 of the multi-phase fluid 102. The rotor member 110 can include any number of threads 202.

In one example embodiment, a thread angle of the plurality of threads 202 is about 5 degrees to about 95°. Specific examples of the thread angle of the threads 202 include about 5°, about 10°, about 20°, about 25°, about 30°, about 35°, about 40°, about 45°, about 50°, about 55°, about 60°, about 65°, about 70°, about 75°, about 80°, about 85°, about 90°, about 95°, and ranges between any two of these values (including endpoints).

The plurality of threads 202 may have any desired configuration. For example, the threads 202 may include acme threads, buttress threads, whitworth threads, V-threads, or combinations thereof. The pitch and depth of the threads 202 may be selected based upon density and viscosity of each of the first phase 106 and the second phase 108 of the multi-phase fluid 102 and a required degree of mixing of the first phase 106 and the second phase 108, or combinations thereof.

In some examples, the pitch of the threads 202 is about 0.1 millimeter (mm) to about 25 mm. Specific examples of pitch of the threads 202 include about 0.1 mm, about 0.5 mm, about 1 mm, about 2.5 mm, about 5 mm, about 7.5 mm, about 10 mm, about 12.5 mm, about 15 mm, about 17.5 mm, about 20 mm, about 22.5 mm, about 25 mm, and ranges between any two of these values (including endpoints). In some examples, a ratio of pitch of the threads 202 to the length of the rotor member 110 is about 0.01 to 0.5. Specific examples of the ratio include about 0.01, about 0.05, about 0.1, about 0.15, about 0.2, about 0.25, about 0.3, about 0.35, about 0.4, about 0.45, about 0.5, and ranges between any two of these values (including endpoints).

In some examples, a depth of the threads 202 is about 0.1 mm to about 25 mm. Specific examples of the depth of the threads include about 0.1 mm, about 1 mm, about 5 mm, about 10 mm, about 15 mm, about 20 mm, about 25 mm, and ranges between any two of these values (including endpoints). In some examples, a ratio of depth and the diameter of the threads 202 is about 0.01 to about 0.5. Specific examples of the ratio of depth and the diameter of the threads 202 include about 0.01, about 0.05, about 0.1, about 0.15, about 0.2, about 0.25, about 0.3, about 0.35, about 0.4, about 0.45, about 0.5, and ranges between any two of these values (including endpoints).

In operation, the rotor member 110 rotates about the horizontal rotational axis 112 to induce shear in the first phase 106 and the second phase 108 of the multi-phase fluid 102 in a plane normal to the rotational axis 112. The rotor member 110 facilitates driving of the first phase 106 and the second phase 108 molecules of the multi-phase fluid 102 proximate a surface of the rotor member 110, to facilitate mixing of the first phase 106 and the second phase 108.

Moreover, as the rotor member 110 is rotated within the static chamber 104, the threads 202 formed on the rotor member 114 facilitate further mixing of the first phase 106 and the second phase 108 of the multi-phase fluid 102. In certain embodiments, a degree of mixing of the first phase 106 and the second phase 108 may be controlled based upon a type of threads formed on the rotor member 110, number of threads and an induced shear rate through the rotor member 110.

Figure 3:
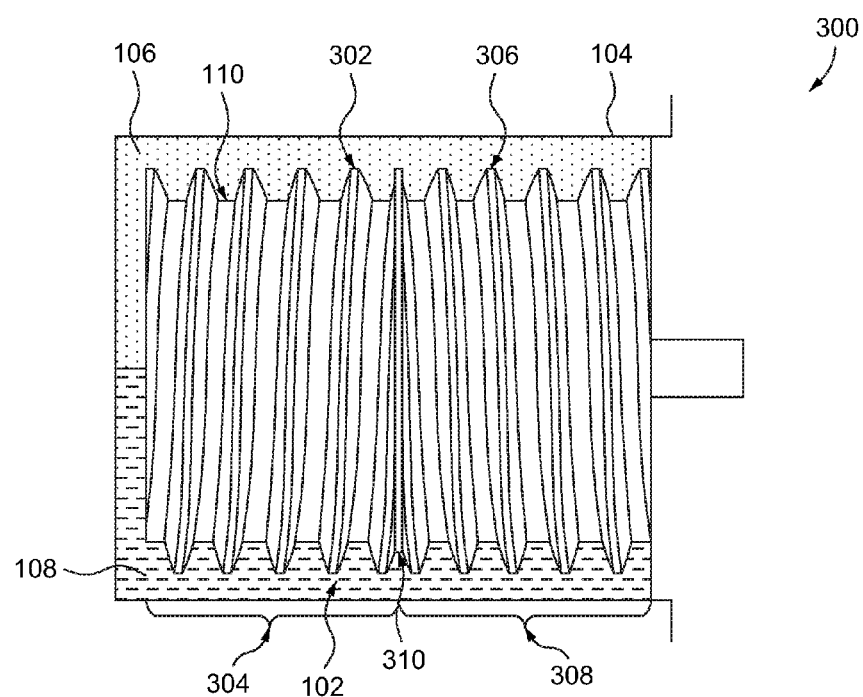
FIG. 3 illustrates an example configuration of the apparatus of FIG. 2 having a rotor member with oppositely angled threads.

FIG. 3 illustrates another example configuration 300 of the apparatus 100 of FIG. 2. As illustrated, the apparatus 300 includes the static chamber 104 configured to contain the multi-phase fluid 102 and the rotor member 110 submersed in the multi-phase fluid 102. In this embodiment, the rotor member 110 includes a first set of threads 302 formed on a first portion 304 of the rotor member 110. Moreover, the rotor member 110 includes a second set of threads 306 formed on a second portion 308 of the rotor member 110. In the illustrated embodiment, the first set of threads 302 and the second set of threads 306 are oppositely angled. Here, a height of the first portion 304 and the second portion 308 having the first set of threads 302 and the second set of threads 306 respectively can be selected based upon a volume of the first phase 106 and the second phase 108 of the multi-phase fluid 102.

In operation, the rotor member 110 is rotated within the static chamber 104 and the first set of threads 302 and the second set of threads 306 formed on the rotor member 110 facilitate mixing of the first phase 106 and the second phase 108 of the multi-phase fluid 102. In particular, the static chamber 104 and the rotor member 110 define a shear zone containing the multi-phase fluid 102. The rotor member 110 rotates about the horizontal rotational axis to apply shear stress to the first phase 106 and the second phase 108 of the multi-phase fluid 102 through the first set of threads 302 and the second set of threads 306. The oppositely angled first and second set of threads 302 and 306 respectively facilitate and enhance the mixing of the first phase 106 and the second phase 108 of the multi-phase fluid 102.

The pitch and depth of the first set of threads 302 and the second set of threads 306 may be selected based upon density and viscosity of each of the first phase 106 and the second phase 108 of the multi-phase fluid 102 and a required degree of mixing of the first phase 106 and the second phase 108, or combinations thereof. In some examples, the pitch of the first set of threads 302 and the second set of threads 306 is about 0.1 millimeter (mm) to about 25 mm. Specific examples of pitch of the first set of threads 302 and the second set of threads 306 include about 0.1 mm, about 0.5 mm, about 1 mm, about 2.5 mm, about 5 mm, about 7.5 mm, about 10 mm, about 12.5 mm, about 15 mm, about 17.5 mm, about 20 mm, about 22.5 mm, about 25 mm, and ranges between any two of these values (including endpoints). In some examples, a ratio of pitch of the first set of threads 302 and the second set of threads 306 to the length of the rotor member 110 is about 0.01 to 0.5. Specific examples of the ratio include about 0.01, about 0.05, about 0.1, about 0.15, about 0.2, about 0.25, about 0.3, about 0.35, about 0.4, about 0.45, about 0.5, and ranges between any two of these values (including endpoints).

In some examples, a depth of the first set of threads 302 and the second set of threads 306 is about 0.1 mm to about 25 mm. Specific examples of the depth of the first set of threads 302 and the second set of threads 306 include about 0.1 mm, about 1 mm, about 5 mm, about 10 mm, about 15 mm, about 20 mm, about 25 mm, and ranges between any two of these values (including endpoints). In some examples, a ratio of depth and the diameter of the first set of threads 302 and the second set of threads 306 is about 0.01 to about 0.5. Specific examples of the ratio of depth and the diameter of the first set of threads 302 and the second set of threads 306 include about 0.01, about 0.05, about 0.1, about 0.15, about 0.2, about 0.25, about 0.3, about 0.35, about 0.4, about 0.45, about 0.5, and ranges between any two of these values (including endpoints).

Figure 4:
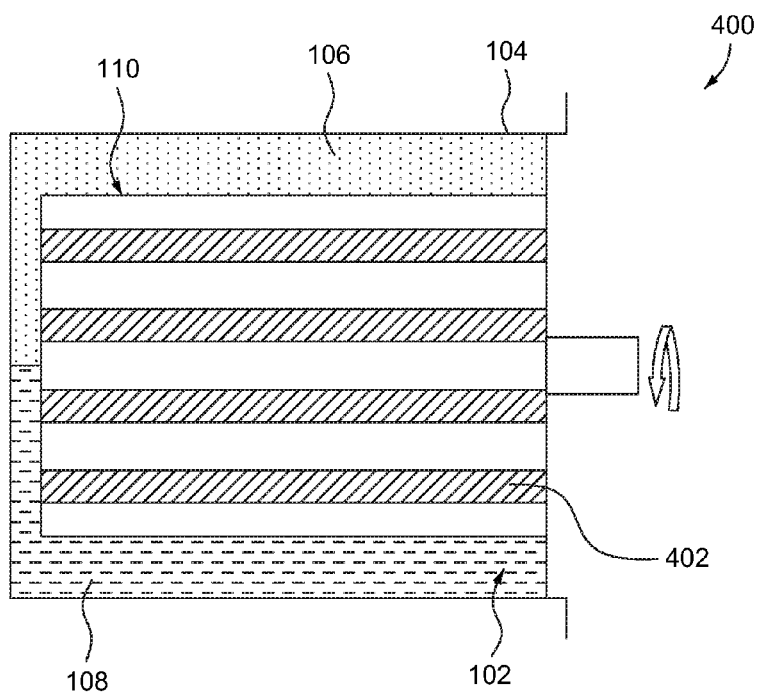
FIG. 4 illustrates an example configuration of the apparatus of FIG. 2 having a rotor member with longitudinal threads.

FIG. 4 illustrates another example configuration 400 of the apparatus 100 of FIG. 2. In this configuration, the rotor member 110 includes a plurality of longitudinal threads generally represented by reference numeral 402 along a horizontal rotational axis of the rotor member 110 to facilitate better mixing of the first phase 106 and the second phase 108 of the multi-phase fluid 102. The plurality of longitudinal threads 402 may have any desired configuration. For example, the threads 402 may include acme threads, buttress threads, whitworth threads, V-threads, semi-circular threads or combinations thereof.

EXAMPLES

The present invention will be described below in further detail with examples and comparative examples thereof, but it is noted that the present invention is by no means intended to be limited to these examples.

Example 1: Computational Fluid Dynamics (CFD) Simulation for Measuring Rheological Properties of a Multi-Phase Fluid Using Example Apparatus of FIG. 1

Figure 5:
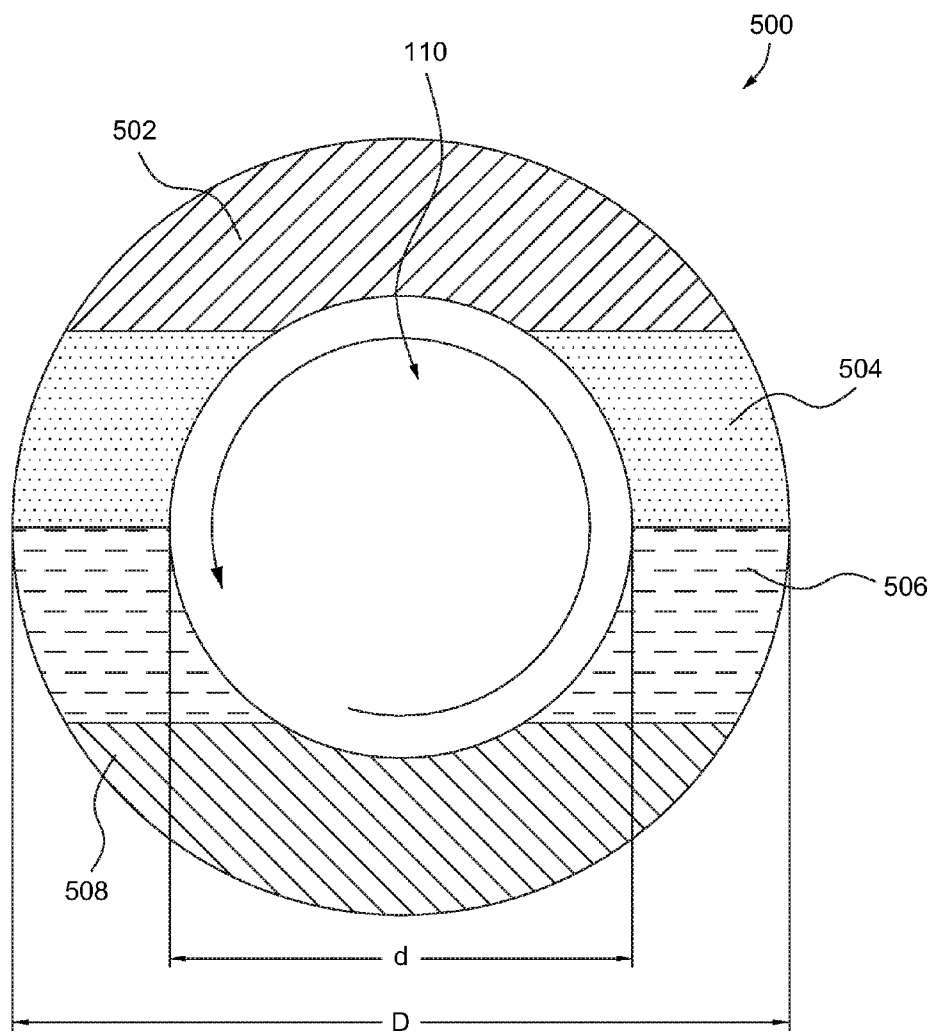
FIG. 5 illustrates a cross-sectional view of the apparatus of FIG. 1 used in a simulation model for measuring rheological properties of a multi-phase fluid.

FIG. 5 illustrates a cross sectional view 500 of an apparatus used in a simulation model for measuring rheological properties of a multi-phase fluid. The CFD simulations were performed using commercially available simulation tools such as Ansys (from Ansys, Inc, USA). Here, two-dimensional (2d) and three-dimensional simulations for a multi-phase fluid were performed using the configuration of the apparatus described above with reference to FIG. 1. It was noted that at low shear rates the cross flow effect and end wall effect were negligible.

Here, two-dimensional CFD simulations were carried out for clearance values of about 1 millimeter (mm) and 10 mm between the static chamber and the rotor member. A structured hexa mesh was generated using O-grid blocking meshing technique. Further, the governing equations for the flow were discretized using second order upwinding based scheme and the equations were solved using a CFD solver. In the simulations, unsteady k-ω SST (shear stress transport) and k-ε realizable turbulent models were used with semi implicit method for pressure linked equation (SIMPLE) algorithm for pressure and velocity coupling.

The multiphase flow was solved using volume fraction method. Explicit scheme was used to solve the volume fraction parameters. Further, a convergence criterion of about $10^{-4}$ was set for velocity components, continuity, k, ε and ω with time step of about 0.0001 seconds considering Courant number criteria. Moreover, gravitational forces were also considered in the simulations.

Here, four fluids (diesel, kerosene, engine oil and water) represented by reference numerals 502, 504, 506 and 508 respectively having different densities were considered in the simulations. The inner diameter of the static chamber 104 and the outer diameter of the rotor member are represented as "D" and "d" respectively. The values of diameters "D" and "d" used for the CFD simulation were about 50 mm and 30 mm respectively. The properties of the fluids used for simulations are provided in Table 1.

TABLE 1

| Fluid (all in liquid state) | Viscosity (Pascal second) | Density (kilogram per cubic meter) |
| --- | --- | --- |
| Diesel | 0.0024 | 730 |
| Kerosene | 0.0024 | 780 |
| Engine oil | 1.06 | 889 |
| Water | 0.001003 | 998.2 |

The viscosity measurements were estimated using the motor torque required to maintain a certain rotational speed of the rotor member in the emulsion. The four fluids 502, 504, 506 and 508 were considered to be settled over one another exhibiting a free surface parallel to the ground due to gravitational effect as shown in FIG. 3. The fluid with highest density (water) was placed at the bottom of the static chamber 104 and the fluid with the lowest density value (diesel) was placed at the top of the static chamber 104. Further, the rotor member 114 was rotated at an angular velocity of about 6 radian per second (rad/sec) and about 60 rad/sec for the simulations corresponding to clearance values of about 1 mm and about 10 mm between the static chamber 104 and the rotor member 110.

Example 2: Results of CFD Simulations for Rheological Properties of the Multi-Phase Fluid of Example 1

As described above, two-dimensional CFD simulations were carried out for clearance values of 1 millimeter (mm) and 10 mm between the static chamber 104 and the rotor member 110. It was observed that for about 1 mm clearance between the static chamber 104 and the rotor member 110, the particle motion was dominated by shear flow. Further, for a clearance value of about 10 mm clearance between the static chamber 104 and the rotor member 110, the particle motion was due to both shear and extensional flows. It was observed that the mixing for immiscible fluids was pronounced for the configuration with the clearance value of about 10 mm between the static chamber 104 and the rotor member 110.

Further, the mixing was observed to be substantially complete in a time period of less than about 1 second for a rotating speed of about 60 rad/sec. It was observed that at higher speed of rotation (e.g., about 60 rad/sec) of the rotor member 110, the mixing of the fluids was achieved in substantially less time due to the dominating extensional flow. Alternately, mixing of the fluids was achieved at both low speed of rotation (for example, about 6 rad/sec) and high speed of rotation (for example, about 60 rad/sec) of the rotor member 110 as the flow was dominated by shear flow.

The mixing pattern of the fluids for a vertical-axis configuration of the apparatus with the static chamber 104 and the rotor member 110 oriented in a generally vertical direction were generated using simulation. The mixing pattern at a rotational speed of about 60 rad/sec of the rotor member for the vertical configuration indicated that the degree of mixing of the fluids at an elapsed time period of about 3 seconds was about 10%. However, it was observed that the degree of mixing of the fluids for the horizontal configuration with the static chamber 104 and the rotor member 110 oriented in a generally horizontal direction was about 95% at an elapsed time period of about 0.7 seconds. Thus, it was seen that the horizontal orientation of the static chamber 104 and the rotor member 110 resulted in significantly more efficient mixing of the fluids as compared to the vertical configuration of the apparatus.

Example 3: Results of Degree of Mixing with Time of the Multi-Phase Fluid Using Example Apparatus of FIG. 1

Figure 6:
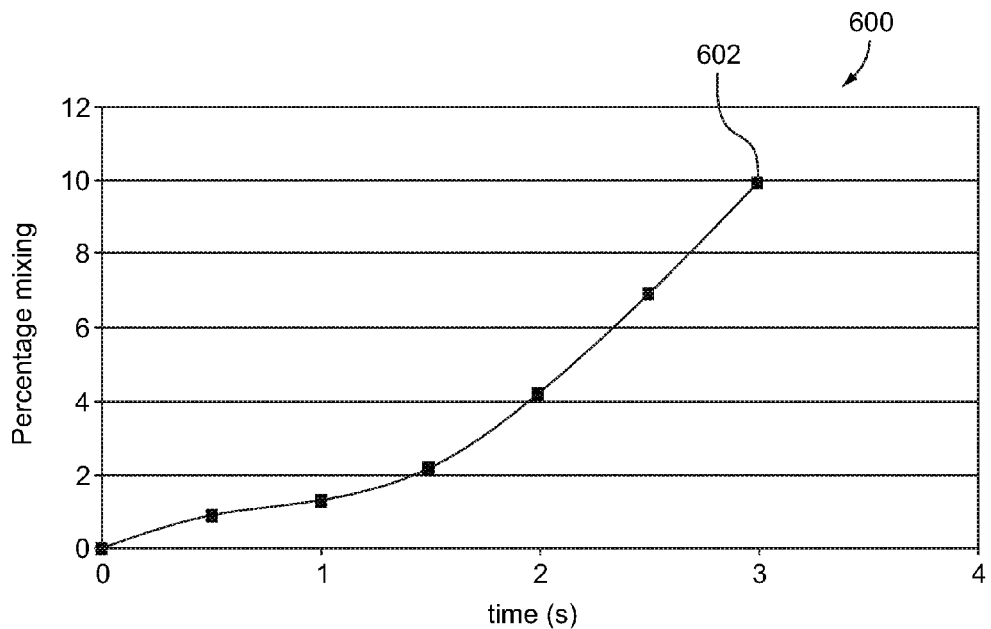
FIG. 6 is a graphical representation illustrating degree of mixing of fluids with time measured using a conventional (vertical-axis) viscometer, for a given fluid system.
Figure 7:
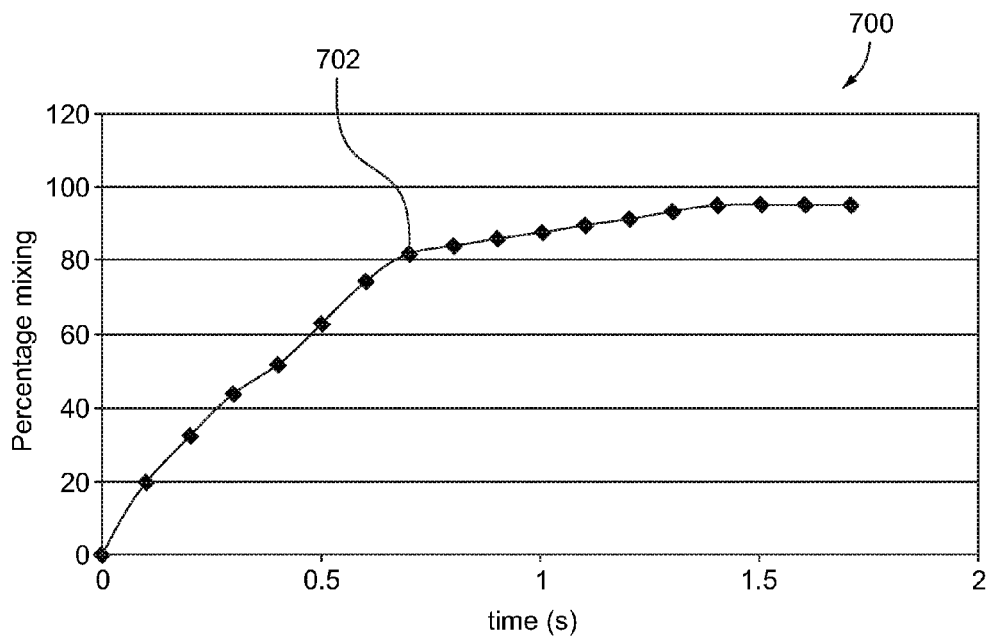
FIG. 7 is a graphical representation illustrating degree of mixing of fluids with time measured using the apparatus of FIG. 1, for a given fluid system.

FIG. 6 and FIG. 7 are graphical representations 600 and 700 illustrating degree of mixing of fluids with time for a conventional viscometer and the apparatus of FIG. 1 respectively. The x-axis is time in seconds, and the y-axis is percentage mixing. Here, four immiscible fluids (diesel, kerosene, engine oil and water) of Example 1 were used for the measurements. The rotor member 110 was rotated at a rotational speed of about 60 revolutions per minute (rpm) within the static chamber.

As can be seen from the example profile 600, the percentage mixing of the fluids increases with time for a conventional viscometer. However, the overall percentage mixing is relatively lower compared to that achieved using the proposed apparatus 100 of FIG. 1. For example, the percentage mixing of the fluids for the conventional viscometer was measured to be about 10% at an elapsed time period of about 3 seconds as shown by reference numeral 602.

However, the percentage mixing of the fluids using the proposed apparatus 100 is substantially higher as compared to that measured using the conventional viscometer. For example, the percentage mixing of the fluids using the apparatus 100 was measured to be about 95% at time period of about 0.7 seconds, as represented by reference numeral 702, indicating substantially high percentage mixing achieved in a short duration. As better mixing facilitates viscosity measurements more representative of those expected in-situ, the horizontally oriented viscometer resulted in substantially accurate measurements of the rheological properties of the fluids.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

As will also be understood by one skilled in the art all language such as "up to," "at least," "greater than," "less than," and the like include the number recited and refer to ranges which can be subsequently broken down into sub ranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. An apparatus for measuring rheological properties of a multi-phase fluid, the apparatus comprising:
a static chamber configured to contain a multi-phase fluid having at least a first phase and a second phase, the static chamber having an inlet port to introduce the multi-phase fluid into the chamber and an outlet port to remove the multi-phase fluid from the static chamber, wherein the inlet port is formed above the outlet port in a vertical direction; and
a rotor member configured to be submersed in the multi-phase fluid contained in the static chamber, wherein at least one of the rotor member and the static chamber is rotatable about a horizontal rotational axis, and wherein the static chamber and the rotor member are oriented in a substantially horizontal direction.

2. The apparatus of claim 1, wherein the rotor member is rotatable about the horizontal rotational axis within the static chamber.

3. The apparatus of claim 1, wherein the static chamber and the rotor member are coaxial.

4. The apparatus of claim 1, wherein at least one of the static chamber and the rotor member is formed of metal, steel, stainless steel, hastelloy, titanium, aluminum, quartz, optical glass, Inconel, acrylic, or combinations thereof.

5. The apparatus of claim 1, wherein the multi-phase fluid comprises at least two immiscible fluids.

6. The apparatus of claim 1, wherein the first phase of the multi-phase fluid is a liquid and the second phase is a gas.

7. The apparatus of claim 1, wherein the first phase of the multi-phase fluid is a solid and the second phase is a liquid.

8. The apparatus of claim 1, wherein the first phase of the multi-phase fluid is a liquid, the second phase is a solid, and a third phase is a gas.

9. The apparatus of claim 1, wherein the rotor member is configured to induce shear in the multi-phase fluid in a plane normal to the rotational axis and to facilitate mixing of the at least first phase and the second phase.

10. The apparatus of claim 1, wherein the rotor member comprises a plurality of longitudinal threads formed on a first surface of the rotor member which extend in the horizontal direction.

11. The apparatus of claim 1, wherein the rotor member comprises a first set of threads formed on a first portion of the rotor member and a second set of threads formed on a second portion of the rotor member, wherein the first set of threads and the second set of threads are oppositely angled.

12. The apparatus of claim 1, wherein the rotor member is configured to rotate about an axis of eccentric or non-eccentric rotation.

13. The apparatus of claim 1, wherein at least one of the static chamber and/or rotor member has a rough surface and the ratio of a measured roughness to a diameter of the static chamber and/or the rotor member is about $10^{-5}$ to about 0.5.

14. The apparatus of claim 1, further comprising a processing circuitry configured to estimate the rheological properties of the multi-phase fluid based on a shear rate, a temperature of the multi-phase fluid, a pressure of the multi-phase fluid, or combinations thereof.

15. The apparatus of claim 14, wherein the rheological properties of the multi-phase fluid comprise a viscosity, a shear storage modulus, a shear loss modulus, or combinations thereof.

16. An apparatus for measuring rheological properties of a multi-phase fluid, the apparatus comprising:
   a static chamber configured to contain a multi-phase fluid having at least a first phase and a second phase, the static chamber having an inlet port to introduce the multi-phase fluid into the static chamber and an outlet port to remove the multi-phase fluid from the static chamber, wherein the inlet port is formed above the outlet port in a vertical direction;
   a rotor member configured to be submersed in the multi-phase fluid in the static chamber and rotatable about a rotational axis within the static chamber to induce shear in the multi-phase fluid in a plane normal to the rotational axis, wherein the static chamber and the rotor member are oriented in a substantially horizontal direction; and
   a processing circuitry configured to estimate the rheological properties of the multi-phase fluid as the rotor member is rotated within the static chamber.

17. The apparatus of claim 16, wherein the multi-phase fluid comprises at least two immiscible fluids.

18. The apparatus of claim 16, wherein the processing circuitry is configured to estimate the rheological properties of the multi-phase fluid based upon an induced shear rate, a temperature of the multi-phase fluid, a pressure of the multi-phase fluid, or combinations thereof.

19. The apparatus of claim 16, wherein the rheological properties of the multi-phase fluid comprise a viscosity, a shear storage modulus, a shear loss modulus, or combinations thereof.

20. A method for measuring rheological properties of a multi-phase fluid, the method comprising:
   providing a static chamber having a rotor member, wherein the static chamber and the rotor member are oriented in a substantially horizontal direction, wherein the static chamber comprises an inlet port to introduce the multi-phase fluid into the static chamber and an outlet port to remove the multi-phase fluid from the static chamber, wherein the inlet port is formed above the outlet port in a vertical direction;
   placing a multi-phase fluid having a first phase and a second phase within the static chamber; and
   rotating the rotor member about a horizontal rotational axis within the static chamber to induce shear in the multi-phase fluid in a plane normal to the rotational axis.

21. The method of claim 20, wherein rotating the rotor member comprises driving molecules of the multi-phase fluid proximate a surface of the rotor member to facilitate mixing of the first phase and the second phase as the rotor member is rotated about the horizontal rotational axis.

22. The method of claim 20, wherein the multi-phase fluid comprises at least two immiscible fluids.

23. The method of claim 20, further comprising rotating the rotor member about an axis of eccentric rotation.

24. The method of claim 20, further comprising estimating the rheological properties of the multi-phase fluid based upon an applied shear rate, a temperature of the multi-phase fluid, a pressure of the multi-phase fluid, or combinations thereof.

25. The method of claim 24, wherein the rheological properties of the multi-phase fluid comprise a viscosity, a shear storage modulus, a shear loss modulus, or combinations thereof.

* * * * *

UNITED STATES PATENT AND TRADEMARK OFFICE
CERTIFICATE OF CORRECTION

PATENT NO. : 9,863,860 B2  
APPLICATION NO. : 14/914499  
DATED : January 9, 2018  
INVENTOR(S) : Khalde et al.

It is certified that error appears in the above-identified patent and that said Letters Patent is hereby corrected as shown below:

In the Specification

In Column 4, Line 5, delete "30 ram," and insert -- 30 mm, --, therefor.

In Column 4, Line 57, delete "first phase 104" and insert -- first phase 106 --, therefor.

In Column 4, Line 57, delete "second phase 106" and insert -- second phase 108 --, therefor.

In Column 7, Lines 25-26, delete "rotor member 114" and insert -- rotor member 110 --, therefor.

In Column 8, Line 60, delete "Ansys, Inc, USA)." and insert -- Ansys, Inc. USA). --, therefor.

In Column 9, Line 45, delete "rotor member 114" and insert -- rotor member 110 --, therefor.

In Column 11, Line 30, delete "recitation no" and insert -- recitation, no --, therefor.

In Column 11, Line 52, delete "general such" and insert -- general, such --, therefor.

In Column 11, Line 57, delete "together A and C" and insert -- together, A and C --, therefor.

In Column 11, Line 60, delete "general such" and insert -- general, such --, therefor.

In the Claims

In Column 12, Line 58, in Claim 4, delete "Inconel," and insert -- inconel, --, therefor.

Signed and Sealed this  
First Day of May, 2018

Andrei Iancu  
*Director of the United States Patent and Trademark Office*